US012174117B2

(12) United States Patent
Farchy et al.

(10) Patent No.: US 12,174,117 B2
(45) Date of Patent: Dec. 24, 2024

(54) FLUORESCENCE AND SCATTER AND ABSORPTION SPECTROSCOPIC APPARATUS WITH A SAPPHIRE TUBE AND METHOD FOR ANALYZING INLINE LOW LEVEL HYDROCARBON IN A FLOW MEDIUM

(71) Applicant: AGAR Corporation, Inc., Houston, TX (US)

(72) Inventors: David Farchy, Bellaire, TX (US); Vikram Siddavaram, Cypress, TX (US); Yonathan Dattner, Calgary (CA)

(73) Assignee: Agrar Corporation Inc., Houston, TX (US)

( * ) Notice: Subject to any disclaimer, the term of this patent is extended or adjusted under 35 U.S.C. 154(b) by 0 days.

(21) Appl. No.: 18/527,064

(22) Filed: Dec. 1, 2023

(65) Prior Publication Data

US 2024/0094124 A1    Mar. 21, 2024

Related U.S. Application Data

(63) Continuation of application No. 17/383,206, filed on Jul. 22, 2021, now Pat. No. 11,885,743.

(51) Int. Cl.
*G01N 21/64*    (2006.01)
*G01N 33/28*    (2006.01)

(52) U.S. Cl.
CPC ............ *G01N 21/64* (2013.01); *G01N 33/28* (2013.01); *G01N 2021/6417* (2013.01);
(Continued)

(58) Field of Classification Search
None
See application file for complete search history.

(56) References Cited

U.S. PATENT DOCUMENTS 4,293,225 A * 10/1981 Wheaton ............ G01N 21/8507
356/417
4,651,010 A * 3/1987 Javan .................. G01N 21/643
436/166

(Continued)

FOREIGN PATENT DOCUMENTS

GB         2089501 A  *  6/1982  ............. G01N 21/53

*Primary Examiner* — David P Porta
*Assistant Examiner* — Djura Malevic
(74) *Attorney, Agent, or Firm* — Craft Chu PLLC; Andrew W. Chu

(57) ABSTRACT

An apparatus and method of inline measurement of low-concentration hydrocarbons overlaps fluorescence, scatter and absorption spectroscopy devices so as to measure scatter and absorption of fluorescing oil and the excited fluorescence itself. The apparatus includes a fitting, an input port, an output port, and a sapphire tube having a hollow interior in fluid connection with the input port and the output port. Flow medium passes through the input port, the sapphire tube, and the output port. The apparatus also includes a light emitter, a first detector, and a second detector. The light emitter can include a lens, an absorption and scatter wavelength emitter, and a fluorescence wavelength emitter. An incident absorption and scatter beam and an incident fluorescence beam from the light emitter and parallel so as to determine free hydrocarbon, dissolved hydrocarbons, and solids in a sample within the sapphire tube.

9 Claims, 15 Drawing Sheets

(52) U.S. Cl.
CPC ............... *G01N 2021/6478* (2013.01); *G01N 2021/6497* (2013.01); *G01N 2201/12* (2013.01)

(56) References Cited

U.S. PATENT DOCUMENTS

| | | | | |
|---|---|---|---|---|
| 4,705,616 | A * | 11/1987 | Andresen | G01N 27/44717 204/603 |
| 4,851,683 | A * | 7/1989 | Yang | G01N 21/73 250/340 |
| 4,994,671 | A * | 2/1991 | Safinya | E21B 49/088 250/339.05 |
| 5,227,135 | A * | 7/1993 | Godec | G01N 21/766 422/52 |
| 5,330,714 | A * | 7/1994 | Godec | G01N 21/766 422/82.07 |
| RE34,782 | E * | 11/1994 | Dandliker | G01N 21/6408 356/318 |
| 5,480,804 | A * | 1/1996 | Niwa | G01N 21/6458 356/417 |
| 5,489,977 | A * | 2/1996 | Winslow | G01N 21/645 356/73 |
| 5,760,900 | A * | 6/1998 | Ito | G01N 15/1434 356/73 |
| 6,369,894 | B1 * | 4/2002 | Rasimas | G01N 21/645 356/417 |
| 6,507,401 | B1 * | 1/2003 | Turner | G01N 21/8507 356/417 |
| 6,563,585 | B1 * | 5/2003 | Rao | G01N 21/645 356/417 |
| 7,099,012 | B1 * | 8/2006 | Crawford | G01N 21/645 356/417 |
| 7,550,746 | B2 * | 6/2009 | Tokhtuev | G01N 21/8507 250/461.1 |
| 8,017,928 | B2 * | 9/2011 | McStay | G01N 21/645 250/559.4 |
| 8,084,756 | B2 * | 12/2011 | Tokhtuev | G01N 21/6402 250/573 |
| 8,881,577 | B1 * | 11/2014 | Agar | E21B 49/005 73/54.06 |
| 9,140,648 | B2 * | 9/2015 | Tokhtuev | G01N 21/645 |
| 9,267,845 | B2 * | 2/2016 | Ichijyo | C02F 1/008 |
| 9,459,244 | B2 * | 10/2016 | Freese | E21B 47/114 |
| 9,612,221 | B2 * | 4/2017 | Xiao | G01N 27/27 |
| 9,857,305 | B2 * | 1/2018 | Tokhtuev | G01N 21/51 |
| 9,863,887 | B2 * | 1/2018 | Babichenko | G01N 21/94 |
| 10,108,161 | B2 * | 10/2018 | Dattner | G01N 21/45 |
| 10,132,752 | B2 * | 11/2018 | Ng | G01N 15/06 |
| 10,739,284 | B2 * | 8/2020 | Murano | H01J 37/244 |
| 10,801,961 | B2 * | 10/2020 | Hatch | G01N 27/4168 |
| 11,119,027 | B2 * | 9/2021 | Sekimoto | G01N 15/14 |
| 11,163,091 | B2 * | 11/2021 | Alabbad | E21B 43/2401 |
| 11,220,893 | B2 * | 1/2022 | Alabbad | E21B 43/16 |
| 11,474,017 | B2 * | 10/2022 | Sekimoto | G01N 21/6486 |
| 2001/0042714 | A1 * | 11/2001 | Gjerde | C12N 15/101 210/656 |
| 2002/0050564 | A1 * | 5/2002 | Birk | G02B 21/06 250/306 |
| 2003/0006385 | A1 * | 1/2003 | Banks | G01N 21/643 250/559.4 |
| 2004/0061051 | A1 * | 4/2004 | Schneiker | H01J 37/073 250/306 |
| 2004/0223882 | A1 * | 11/2004 | Bonne | G01N 21/67 422/82.11 |
| 2005/0056313 | A1 * | 3/2005 | Hagen | B01F 25/3132 137/3 |
| 2005/0142035 | A1 * | 6/2005 | Bonne | B82Y 10/00 422/82.05 |
| 2006/0250606 | A1 * | 11/2006 | Kaye | G01N 15/0211 356/417 |
| 2007/0046256 | A1 * | 3/2007 | Kim | H02J 7/0042 320/109 |
| 2008/0030712 | A1 * | 2/2008 | Tokhtuev | G01N 21/8507 356/417 |
| 2008/0203332 | A1 * | 8/2008 | McStay | G01N 21/645 250/552 |
| 2009/0122311 | A1 * | 5/2009 | Kanda | G01N 21/645 356/318 |
| 2010/0182606 | A1 * | 7/2010 | Prenner | G01N 21/0332 250/576 |
| 2011/0127444 | A1 * | 6/2011 | Ozasa | G01N 15/1433 356/336 |
| 2012/0227470 | A1 * | 9/2012 | Gerhardt | G01N 30/20 73/61.56 |
| 2012/0292508 | A1 * | 11/2012 | Terauchi | H01J 37/244 250/310 |
| 2013/0036588 | A1 * | 2/2013 | Agar | F16L 41/00 29/428 |
| 2014/0264077 | A1 * | 9/2014 | Tokhtuev | G01N 21/49 250/226 |
| 2014/0335557 | A1 * | 11/2014 | Ichijyo | G01J 3/4406 435/288.7 |
| 2015/0059446 | A1 * | 3/2015 | Agar | G01N 11/08 73/54.02 |
| 2016/0033407 | A1 * | 2/2016 | Tokhtuev | G01N 21/49 250/459.1 |
| 2016/0054285 | A1 * | 2/2016 | Freese | G01N 21/255 356/70 |
| 2016/0306367 | A1 * | 10/2016 | Dattner | G01N 15/0211 |
| 2016/0327683 | A1 * | 11/2016 | Donzier | E21B 49/10 |
| 2016/0341038 | A1 * | 11/2016 | AbuAli | E21B 49/08 |
| 2017/0086760 | A1 * | 3/2017 | Kim | A61C 9/004 |
| 2018/0100862 | A1 * | 4/2018 | Goix | G01N 33/6887 |
| 2019/0049396 | A1 * | 2/2019 | Murano | G01N 23/2252 |
| 2019/0257200 | A1 * | 8/2019 | AbuAli | G01V 9/007 |
| 2019/0310179 | A1 * | 10/2019 | Sekimoto | C12M 31/02 |
| 2021/0063297 | A1 * | 3/2021 | Sekimoto | G01N 15/06 |
| 2021/0088513 | A1 * | 3/2021 | Antognozzi | C12Q 1/00 |
| 2022/0026360 | A1 * | 1/2022 | Farchy | G01N 21/64 |

\* cited by examiner

FLUORESCENCE AND SCATTER AND ABSORPTION SPECTROSCOPIC APPARATUS WITH A SAPPHIRE TUBE AND METHOD FOR ANALYZING INLINE LOW LEVEL HYDROCARBON IN A FLOW MEDIUM

CROSS-REFERENCE TO RELATED APPLICATIONS

The present application claims priority under 35 U.S.C. Section 120 from U.S. patent application Ser. No. 17/383,206, filed on 22 Jul. 2021, entitled "FLUORESCENCE AND SCATTER AND ABSORPTION SPECTROSCOPIC APPARATUS WITH A SAPPHIRE TUBE AND METHOD FOR ANALYZING INLINE LOW LEVEL HYDROCARBON IN A FLOW MEDIUM". See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to inline measurement of hydrocarbons in solution. In particular, the present invention relates to inline measurement of low level concentrations of hydrocarbons. More particularly, the present invention relates to hydrocarbon measurement by fluorescence, scatter, and absorption.

2. Description of Related Art Including Information Disclosed Under 37 CFR 1.97 and 37 CFR 1.98

In modern oil and gas industries and other industries, clean water disposal can be a key element in environmental regulation. Inline instruments to detect the amount of hydrocarbon in water are needed to confirm that the fluid flow is proper for clean water disposal. Current inline instruments are mainly optical and suffer from unreliable readings due to a coating build up on the optical lenses and turbidity caused by particles flowing with the water. There is a need to address these problems for detecting low level concentrations of hydrocarbons in a fluid flow.

There is a myriad of other applications, besides oil and gas production, in which it is useful to measure the concentration of hydrocarbons in water. For example, measuring trace amounts of oil in water during wastewater discharge, e.g. from ships, tankers, municipal and industrial water treatment plants, is very important for mitigating environmental and health concerns. Another application involves monitoring the presence of bacteria in potable water. Some techniques that have been proposed are fluorescence spectroscopy, scatter spectroscopy, and absorption spectroscopy.

When electromagnetic radiation is incident on a sample, some radiation is scattered, some radiation is absorbed, and some radiation is emitted. Fluorescence spectroscopy uses a beam of light as radiation to excite the electrons in molecules of certain compounds. These molecules emit light, usually at a higher wavelength than the beam of light to excite the electrons. That emitted light is directed towards a filter and onto a detector for measurement and identification of the chemical compound or changes in the chemical compound. For hydrocarbons, the molecules can be undissolved or dissolved. The term "free hydrocarbon" also refers to undissolved hydrocarbon. Free hydrocarbon can occur when the solvent is saturated or when the liquids have high interfacial tension, e.g. oil and water. Fluorescence spectroscopy excites all fluorescent hydrocarbon molecules so both free and dissolved hydrocarbons are detected.

Scatter spectroscopy and absorption spectroscopy both measure the change in spectrum of a beam of light that passes through a sample to identify the composition of the sample. Scatter spectroscopy refers to the measurement of light that is scattered by a solid particle or liquid droplet or gas bubble. Scatter spectroscopy is affected by the concentration, shape, size and size distribution of solid particles, liquid droplets or gas bubbles in the sample. The free hydrocarbon would be detected as a liquid droplet within the sample. Scatter spectroscopy is relatively unaffected by dissolved components in the sample. Thus, scatter spectroscopy would relative unaffected by the dissolved hydrocarbons in the sample. Absorption spectroscopy refers to the measurement of light that is absorbed by the sample. Absorption spectroscopy is affected by dissolved components, like dissolved hydrocarbons in the sample. Other dissolved materials, such as solids and salts, would also affect absorption spectroscopy. Free (undissolved) hydrocarbons and undissolved solids, such as wax, also affect absorption spectroscopy, but to a different degree than fluorescence spectroscopy and scatter spectroscopy.

As separate measuring devices, fluorescence, scatter and absorption spectroscopy devices are each rendered unreliable as inline instruments in the oil and gas industry. Coatings on lenses emitting the radiation or light and turbidity in the sample reduce reliability of each spectroscopy device. There is a need to overcome these obstacles. There is a need to overlap fluorescence, scatter and absorption spectroscopies results in a system for reliable independent measurement of free hydrocarbons, dissolved hydrocarbons, and solids.

In the present invention, the apparatus and method overlap the fluorescence, scatter and absorption spectroscopy devices so as to measure scatter and absorption of fluorescing oil and the excited fluorescence itself. An unfiltered detector directly in front of and across from the light source of the spectroscopy devices will drop scatter and absorption measurements as the water gets dirty due to the presence of free (undissolved hydrocarbon, oil) or solid particles (turbidity). The scatter and absorption measurements from the unfiltered detector directly in front of and across from the light source decreases as oil concentration (ppm) increases. The fluorescence measurements increase from the unfiltered detector directly in front of and across from the light source because there is more oil and more fluorescing. A UV filtered detector at 90 degrees from the light source can block UV incident light, while still detecting excitation light from fluorescence. The fluorescence measurements from the filtered detector also increase as the oil concentration (ppm) increases. There is more oil and more fluorescence.

Now as oil concentration increases, there is another effect revealed by the present invention. When oil droplet diameters are much smaller than the near infrared (NIR) light wavelengths of the scatter and absorption spectroscopy devices, the scatter and absorption measurements at the UV filtered detector will increase with oil concentration. Once oil droplet diameters are bigger than the NIR light wavelengths, the scatter and absorption measurements will decrease with increased oil concentration. The fluorescence measurements from the filtered detector increasing, even as the scatter and absorptions measurement decrease can be used to determine free hydrocarbons, dissolved hydrocarbons, and solids. The fluorescence measurements determine free (undissolved) hydrocarbons and dissolved hydrocarbons, while the scatter and absorption measurements determine the free (undissolved) hydrocarbons and solids. The effect of NIR light as scatter and absorption spectroscopy on fluorescing free hydrocarbon and dissolved hydrocarbon in the present invention allow the calculation of free hydrocarbons, dissolved hydrocarbons, and solids.

BRIEF SUMMARY OF THE INVENTION

Embodiments of the invention include a apparatus and method of inline measurement of low-concentration (ppm to ppt level) hydrocarbons. In the present invention, the apparatus and method overlap the fluorescence, scatter and absorption spectroscopy devices so as to measure scatter and absorption of fluorescing oil and the excited fluorescence itself. An unfiltered detector directly in front of and across from the light source of the spectroscopy devices will drop scatter and absorption measurements as the water gets dirty due to the presence of free (undissolved hydrocarbon, oil) or solid particles (turbidity). The scatter and absorption measurements from the unfiltered detector directly in front of and across from the light source decreases as oil concentration (ppm) increases. The fluorescence measurements increase from the unfiltered detector directly in front of and across from the light source because there is more oil and more fluorescing. A UV filtered detector at 90 degrees from the light source can block UV incident light, while still detecting excitation light from fluorescence. The fluorescence measurements from the filtered detector also increase as the oil concentration (ppm) increases. There is more oil and more fluorescence.

Now as oil concentration increases, there are other effects revealed by the present invention. The overlap of the first and second detectors for both the scatter and absorption measurements and the fluorescence measurements allowed the determination of the free hydrocarbon, dissolved hydrocarbon, and solids. When oil droplet diameters are much smaller than the near infrared (NIR) light wavelengths of the scatter and absorption spectroscopy devices, the scatter and absorption measurements at the UV filtered detector will increase with oil concentration. Once oil droplet diameters are bigger than the NIR light wavelengths, the scatter and absorption measurements will decrease with increased oil concentration. The fluorescence measurements from the filtered detector increasing, even as the scatter and absorptions measurement decrease, can be used to determine free hydrocarbons, dissolved hydrocarbons, and solids. The fluorescence measurements determine free (undissolved) hydrocarbons and dissolved hydrocarbons, while the scatter and absorption measurements determine the free (undissolved) hydrocarbons and solids in a desired ratio depending on NIR wavelength. The effect of NIR light as scatter and absorption spectroscopy on fluorescing free hydrocarbon and dissolved hydrocarbon in the present invention allow the calculation of free hydrocarbons, dissolved hydrocarbons, and solids.

Embodiments of the present invention include a sapphire tube, a light emitter having lens, a first detector, and a second detector. There can also be a cleaning apparatus, which can be actuated mechanically or otherwise. The light emitter, first detector, and second detector, as the measurement system, utilizes fluorescence, absorption, and scatter to measure the concentration of hydrocarbons (e.g. ethylene, diesel, crude oil, dyes, asphaltenes) in a medium comprised of water. The transmitted power of the light emitter can vary depending on the status of the lens, i.e. how dirty or coated the lens is. The transmitted power from the lens is measured and used to correct the fluorescence/scatter/absorption energy levels. Thus, the measurement system automatically compensates for the dirt on the lens in real-time. The cleaning apparatus is provided to clear the lens, when transmitted power reaches a pre-determined level. Additionally, the positioning and quantity of the first and second detectors around the sapphire tube allows for compensation due to turbidity and for measurement of two or more solutes (e.g. free vs dissolved hydrocarbons, hydrocarbon A vs hydrocarbon B). The hydrocarbon can be free (undissolved) or dissolved in the water and the water itself can have dissolved solids (such as salts) or free solids (e.g. sand, dirt). Although predominantly described in terms of detecting hydrocarbons in water, the present invention includes an apparatus and method for detecting and quantifying the presence of component A in a medium of component B (which itself can be a mixture of two or more chemical compounds).

By utilizing fluorescence/scatter/absorption spectroscopy, the current invention allows for detection and measurement of certain hydrocarbons which are not fluorescent, e.g. many aliphatic hydrocarbon, and differentiation of free hydrocarbon out of the total solution, e.g. free oil and dissolved oil and water. The present invention improves the reliability and accuracy of the measurements.

DETAILED DESCRIPTION OF THE INVENTION

Figure 1:
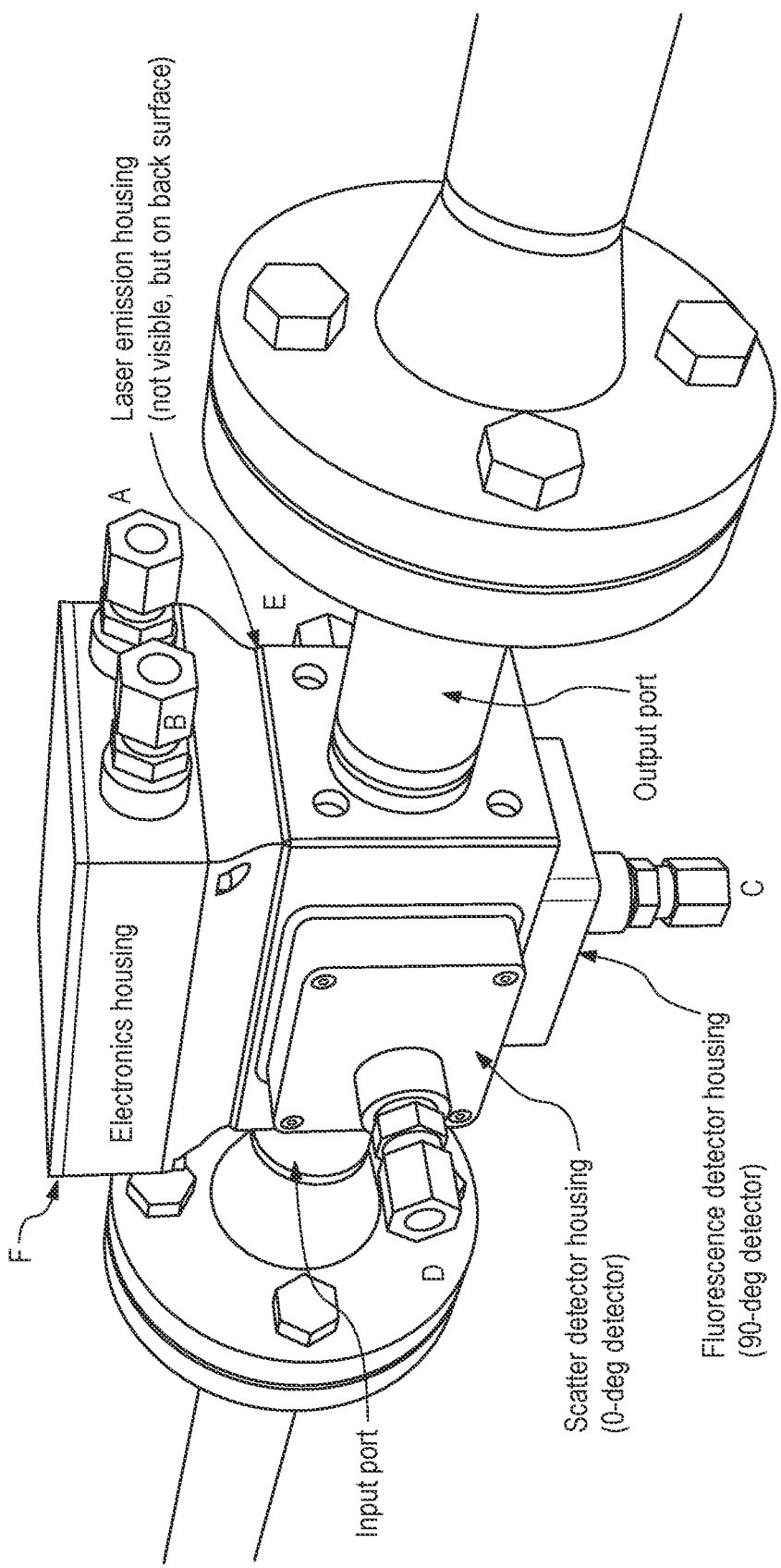
FIG. 1 shows a perspective view of a spectroscopic apparatus according to an exemplary embodiment of the invention.
Figure 2:
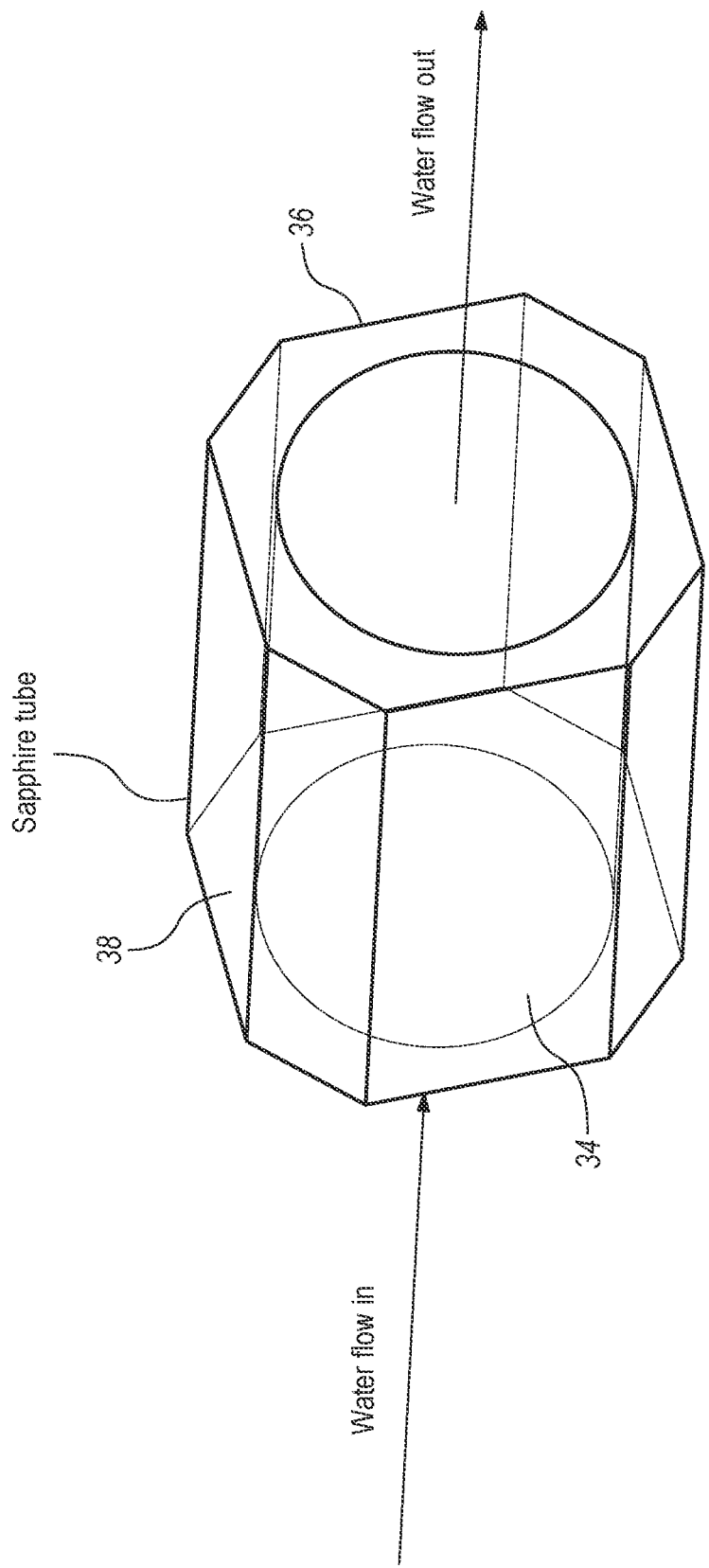
FIG. 2 shows a perspective view of a sapphire tube for the spectroscopic apparatus according to an exemplary embodiment of the invention.
Figure 3A:
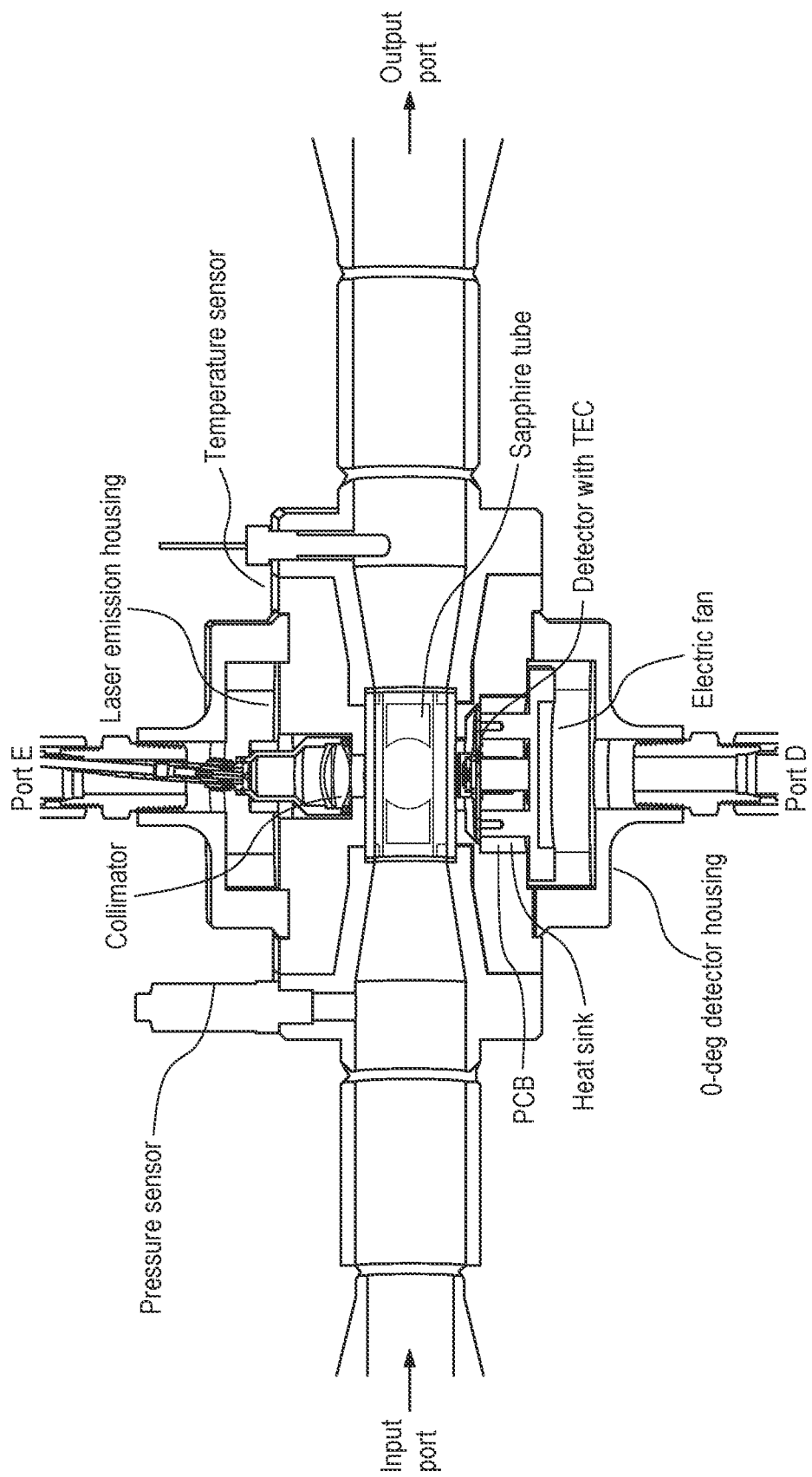
FIG. 3a is a sectional view of the apparatus of FIG. 1.
Figure 3B:
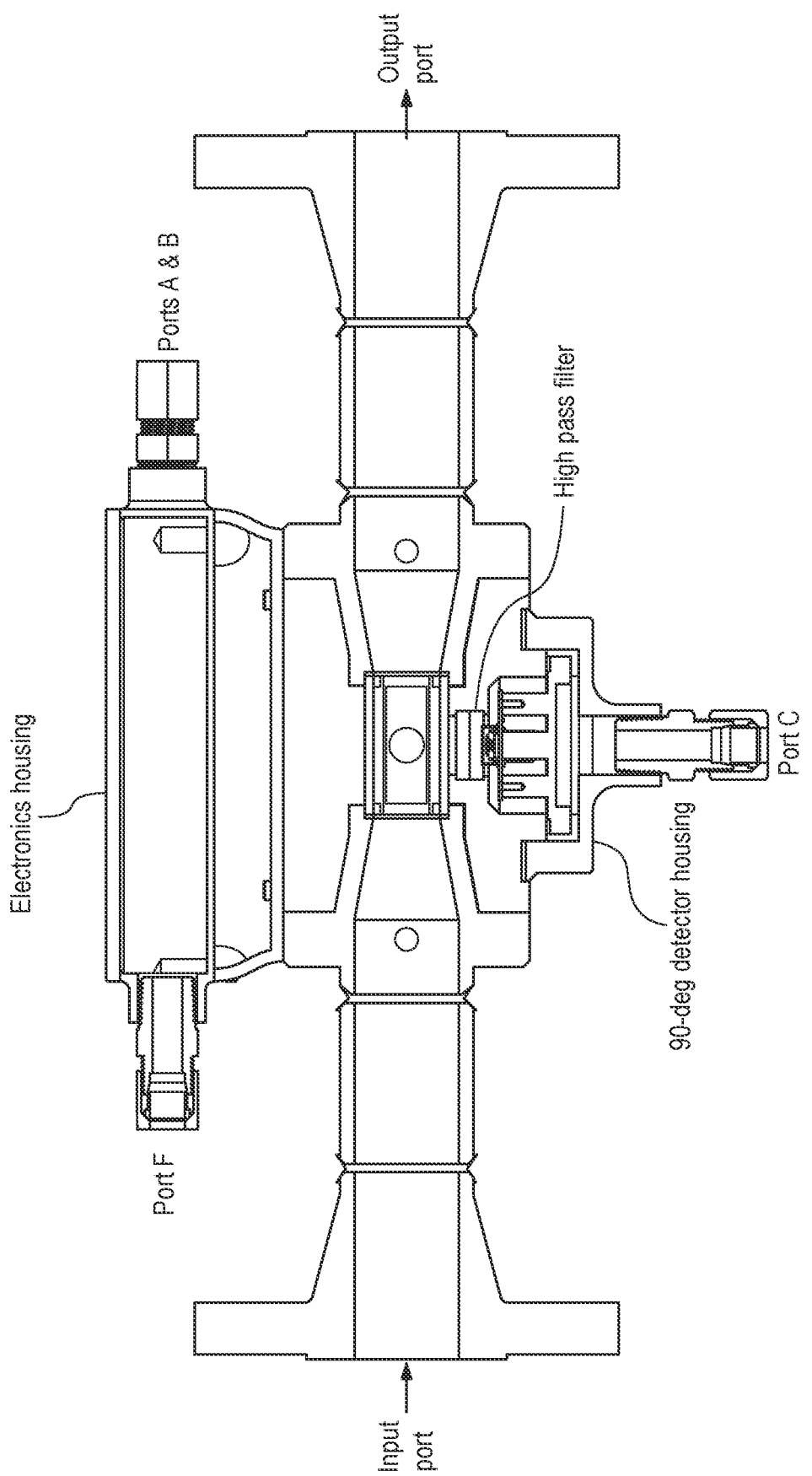
FIG. 3b is another sectional view of the apparatus of FIG. 1.
Figure 4:
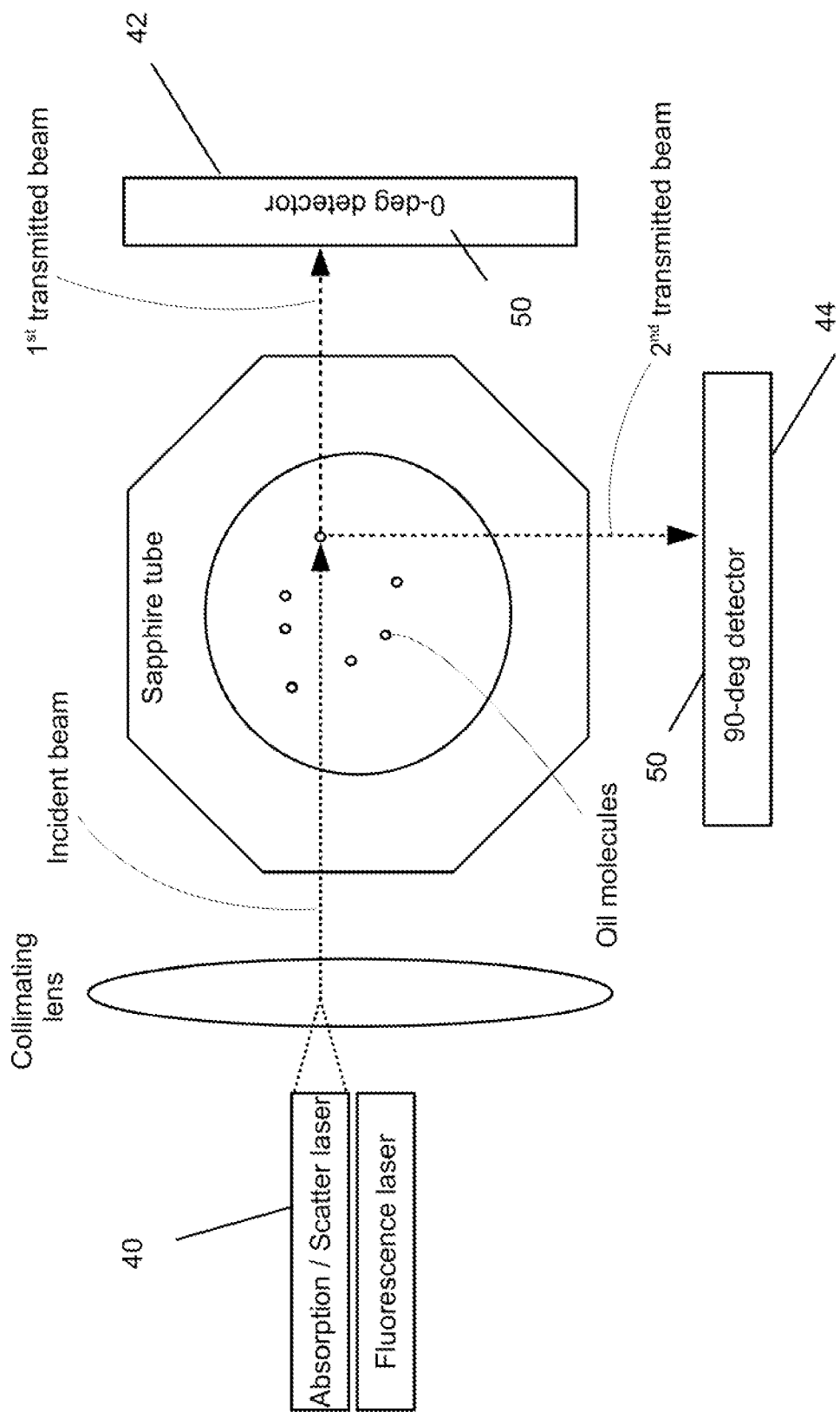
FIG. 4 is a schematic illustration of the method of the present invention.
Figure 13:
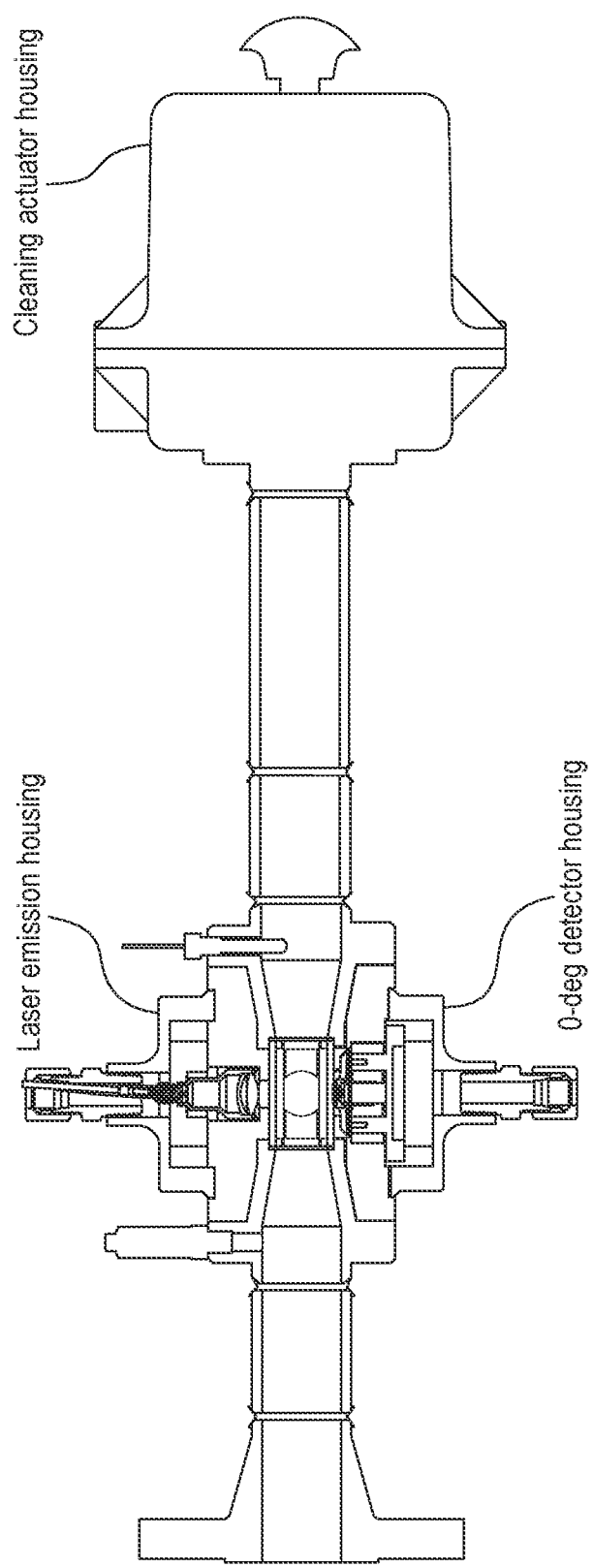
FIG. 13 is a sectional view of a first cross section of the embodiment of FIG. 12 taken along the horizontal plane.
Figure 14:
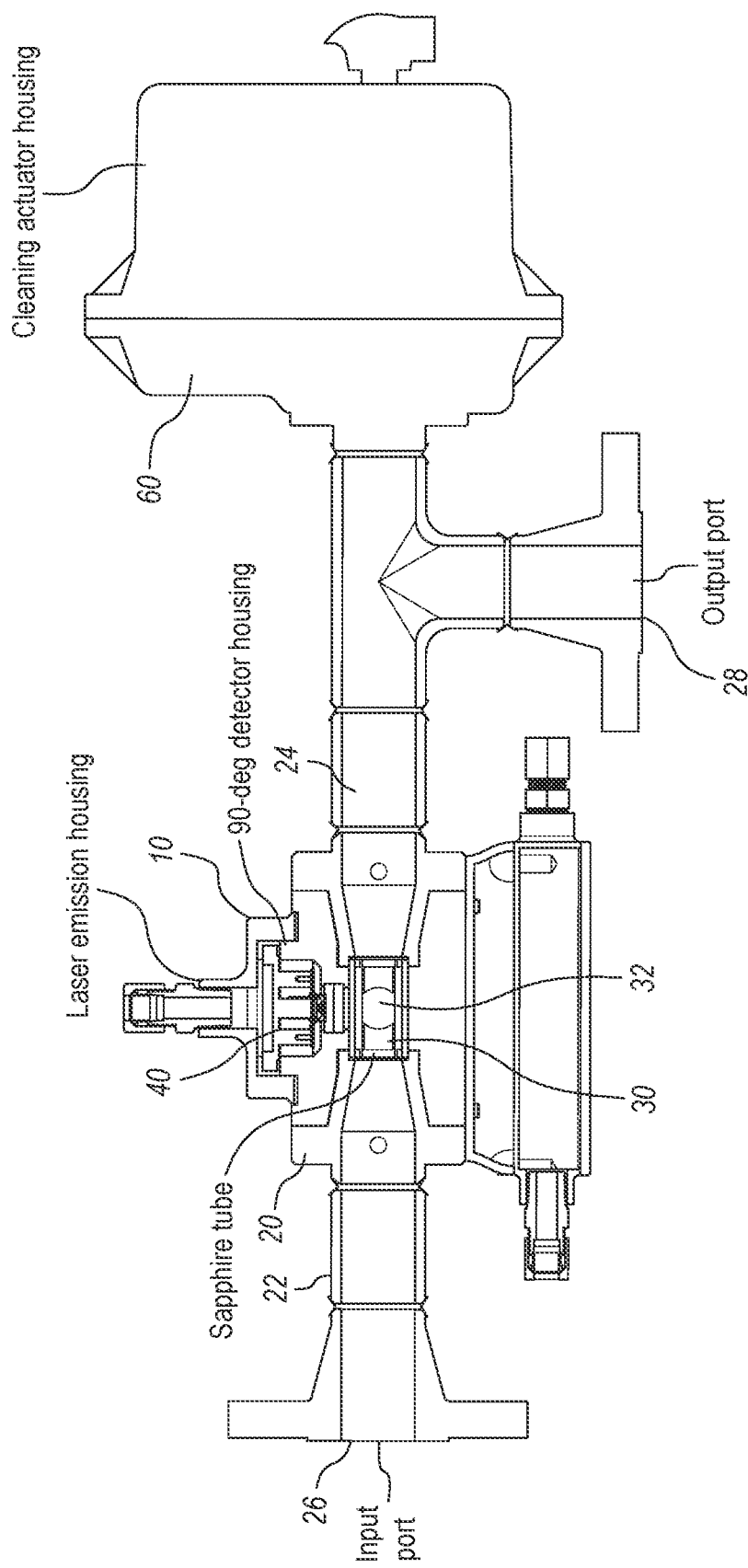
FIG. 14 is a sectional view of a second cross section of the embodiment of FIG. 12 taken along the vertical plane.

Embodiments of the apparatus 10 for detecting hydrocarbon in a flowing medium are shown in FIGS. 1-15, particularly FIGS. 2, 4, and 14. The apparatus 10 includes a fitting 20 having an input end 22 and an output end 24 opposite the input end. There is an input port 26 at the input end and an output port 28 at the output end. A sapphire tube 30 has a hollow interior 32 in fluid connection with the input port and the output port. Flow medium passes through the input port, the sapphire tube, and then the output port. The sapphire tube has a first outer side 34, a second outer side 36 opposite the first outer side, and a third outer side 38 between the first outer side 34 and the second outer side 36. The sapphire tube 30 has a cross section selected from one of a group consisting of: circular, square, rectangular and oval.

The apparatus includes a light emitter 40 coupled to the first outer side, a first detector 42 coupled to the second outer side; and a second detector 44 coupled to the third outer side. The light emitter 40 is comprised of a lens 40A, an absorption and scatter wavelength emitter 40B, and a fluorescence wavelength emitter 40C parallel to the absorption and scatter wavelength emitter. The lens 40A can be a collimator or collimating lens.

The absorption and scatter wavelength emitter is positioned across from the first detector and offset to the second detector so as to emit an incident absorption and scatter beam (incident beam of FIG. 4) through the sapphire tube, the first detector receiving a first absorption and scatter transmitted beam (1st transmitted beam in FIG. 4) from the incident absorption and scatter beam, the second detector receiving a second absorption and scatter transmitted beam (2nd transmitted beam in FIG. 4) from the incident absorption and scatter beam.

The fluorescence wavelength emitter is positioned across from the first detector and offset to the second detector so as to emit an incident fluorescence beam (in FIG. 5) through the sapphire tube, the first detector receiving a fluorescence transmitted beam (transmitted beam in FIG. 5) from the incident fluorescence beam, the second detector receiving a fluorescence excited beam (fluorescence light in FIG. 5) from the sapphire tube. The absorption and scatter wavelength emitter can be positioned orthogonal to the second detector. The incident absorption and scatter beam is parallel to the incident fluorescence beam so as to determine free hydrocarbon, dissolved hydrocarbons, and solids in a sample within the sapphire tube. Alternative embodiments include additional outer sides at various degrees of separation from each other, and corresponding detector devices. For example, a fourth outer side can be perpendicular to the first outer side and across from the third outer side.

In the present invention, the incident absorption and scatter beam has a different wavelength than the incident fluorescence beam. The incident absorption and scatter beam wavelength is in near infrared (NIR) range, while the incident fluorescence beam wavelength is ultraviolet (UV) or excites UV light to be generated by hydrocarbon molecules. The first detector and the second detector are positioned around the sapphire tube so as to simultaneously receive the first absorption and scatter transmitted beam, the second absorption and scatter transmitted beam, the fluorescence transmitted beam, and the fluorescence excited beam.

Figure 6:
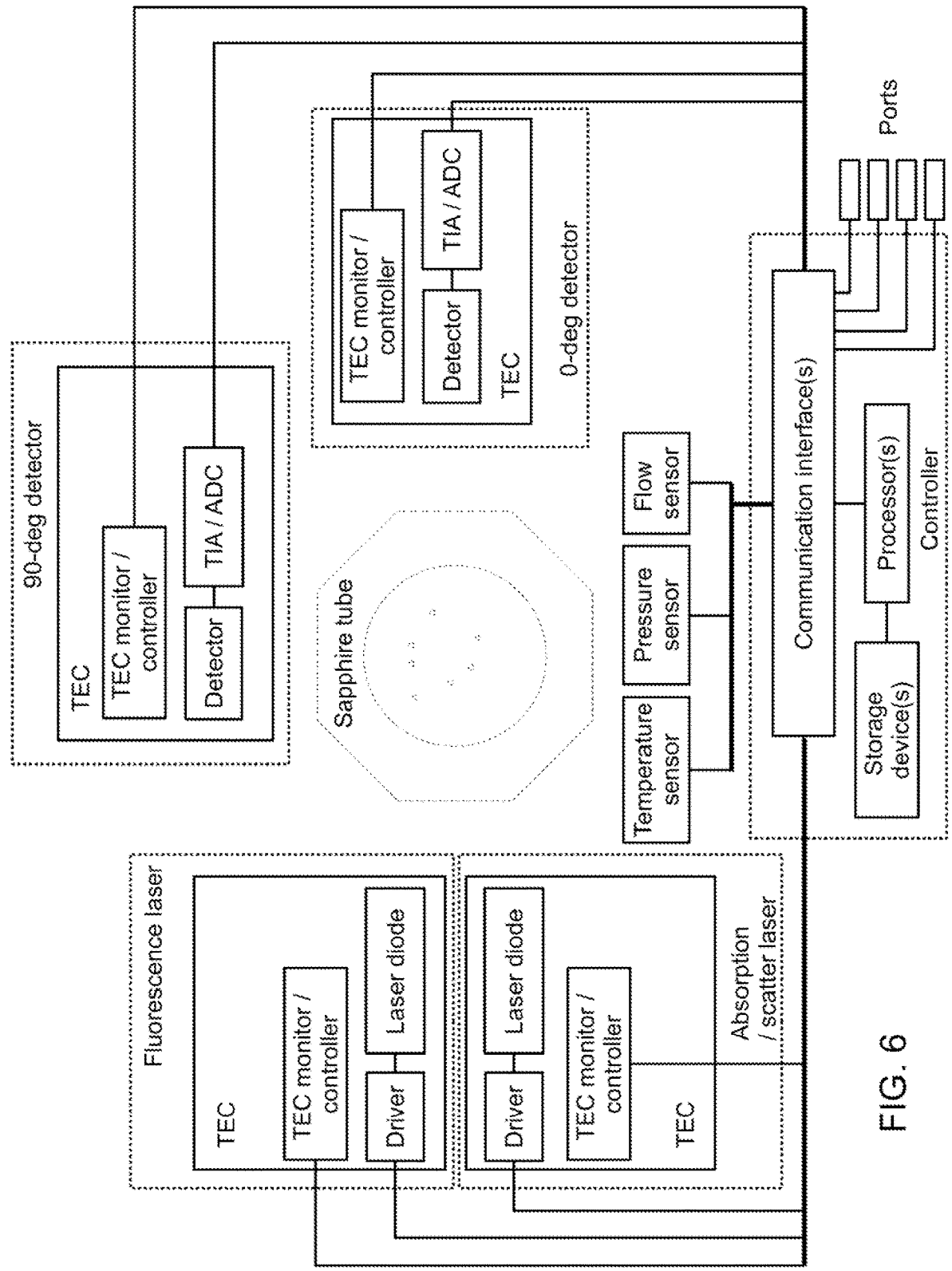
FIG. 6 is a schematic illustration of the apparatus and method of the present invention.

Embodiments in FIGS. 1, 3b, and 6 show the apparatus 10 having an electronics housing being comprised of a central processing unit. The light emitter, the first detector, and the second detector are in communication with the central processing unit. In some embodiments, the electronics housing is further comprised of a fiber optic cable connected to the light emitter. There can also be the embodiments of FIGS. 3a and 6 including a temperature sensor in communication with the central processing unit; and a pressure sensor in communication with the central processing unit. FIG. 3a also shows the first detector comprising a fan, a heat sink and a control module. The control module is comprised of a printed circuit board. The first detector can also have a thermoelectric cooler.

As in FIGS. 10-15, the invention also includes embodiments having a cleaning apparatus removably engaged with the sapphire tube through the outlet end of the fitting. The cleaning apparatus is comprised of a cleaning head and a telescopic actuator. The telescoping actuator has a retracted position and an extended position. The cleaning head is in contact with the hollow interior of the sapphire tube so as to clean an interior surface of the sapphire tube when the telescopic actuator moves between the retracted position and the extended position. Alternatively, the cleaning apparatus has an extended position within the sapphire tube so as to remove material from the hollow interior facing the first outer side, the second outer side, and the third outer side and the light emitter. The cleaning apparatus is also in removable engagement with the lens of the light emitter so as to remove a coating from the lens. The cleaning apparatus can be ultrasonic or mechanical.

The invention is not limited to pure water solutions as the flow medium. Concentrations of hydrocarbons in brines (consisting of multiple salts and minerals such as NaCl, KCl, K2SO4 etc.) are compatible with the apparatus. Additionally, concentrations of hydrocarbons in water with solids, such as solid particles like sand, can be measured. The apparatus also distinguishes between dissolved components and non-dissolved or free components. The hydrocarbons, like oil, can be dissolved or free in the flow medium. Any solid particles can also be dissolved or free in the flow medium.

The invention can easily be extended to detection of multiple hydrocarbons (e.g. Crude Oil A and Crude Oil B in saltwater) by using more than two wavelengths or even sweeping the wavelengths as needed.

The detectors are not limited to 0 degree and 90-degree orientations, even if outer sides are not equally positioned around the hollow interior. More detectors can be added to increase the accuracy and reliability of the measurement.

The hydrocarbon does not have to be fluorescent. By relying on fluorescence spectroscopy and scatter/absorption spectroscopy, the invention can detect nonfluorescent components, e.g. aliphatic hydrocarbons as well.

Embodiments of the present invention include circular and non-circular cross section so the hollow interior of the sapphire tube. Other configurations, such as rectangular, square or oval cross sections, can be accommodated in the present invention.

FIG. 1 shows a perspective view of a spectroscopic apparatus according to an exemplary embodiment of the invention. In this embodiment, the apparatus is rectangular in shape and has an input port and an output port on the front end and side end, respectively. The top side of the apparatus includes an electronics housing within which multiple electronic components are located. As shown in FIG. 1, the explosion proof and waterproof electronics housing includes three ports A, B and F.

The apparatus further includes a light beam emission housing having a port E attached to one side of the apparatus as illustrated in FIG. 1. Opposite, there is a scatter detector housing with port D attached thereto. Finally, on the bottom side, there is a fluorescent detector with port C attached thereto. In some embodiments, both detectors are simultaneously utilized to detect light in both modes (scatter & fluorescence); thus, these detectors are also referred to as the 180-deg or 0-deg detector (in-line with the light beam) and the 90-deg detector (perpendicular to the emitted light beam). Both the components and the ports A-F are described further in the following.

FIG. 2 illustrates a sapphire tube that is in the middle of the apparatus and through which the fluid mixture flows when passing from the input port to the output port. As shown, the sapphire tube has a hexagonal outside surface and a circular inner surface, in this embodiment.

FIG. 3a illustrates a cross-sectional view of the apparatus of FIG. 1 taken along the horizontal plane of FIG. 1. FIG. 3b illustrates a cross-sectional view of the apparatus of FIG. 1 taken along the vertical plane of FIG. 1. Fluid mixture flows into the apparatus via the input port, passes through the sapphire tube in the middle, and then flow out of the apparatus via the output port.

The light emission housing includes a collimator to ensure the light beam received via port E is emitted as a parallel beam of rays into the water via a first side of the sapphire tube wall. The actual light beam in this embodiment is provided via a fiber optic cable that is connected to port E. In this embodiment, the light beam is generated within the electronics housing of the apparatus where it is thereafter outputted on port F and transmitted to the light emission housing via a fiber optic cable connected between ports E and F.

Opposite the light emission housing, the scatter detector housing includes a detector, the detectors are design to be stable in time and temperature. For example, in one embodiment is mounted on a thermoelectric cooler (TEC) in turn mounted on a printed circuit board (PCB). The PCB in this embodiment is aluminum nitride (AlN) ceramic board to thereby facilitate good heat transfer from the top side to the bottom side of the PCB. In this embodiment, a heat sink transfers heat away from the PCB board and an electric fan provides air flow to cool the heat sink. Electric power for the detector, TEC, and fan is provided via port D.

Other way to get the detector reading accurately is to compensate the reading base on temperature curve or base on reference light detected.

FIG. 4 illustrates a simplified cross-sectional view of the apparatus of FIG. 1 taken along a plane running vertical through the center of the apparatus perpendicular to the flow of water while the apparatus is operating in a first light mode. In this embodiment, the first light mode corresponds to an absorption/scatter light. The wavelength of the absorption/scatter light is optimized for the fluid mixture being measured. The wavelength is a selected absorption and scatter wavelength for targeted absorption measurements. For the present embodiment of detecting high API crude oil-in-water, the wavelength is in the 780 nm range. The collimating lens of the collimator ensures the beam is formed of parallel rays that pass through a first side of the sapphire tube. When the beam impacts a molecule of free oil in the water, a portion of the wavelengths is absorbed. Thus, the spectra of the incident beam passing through a second side of the sapphire tube (opposite the first side) differs from the transmitted beam, which is detected by the 0-deg detector. Likewise, there is a 2nd transmitted beam that may be emitted toward and detected by the 90-deg detector.

Figure 5:
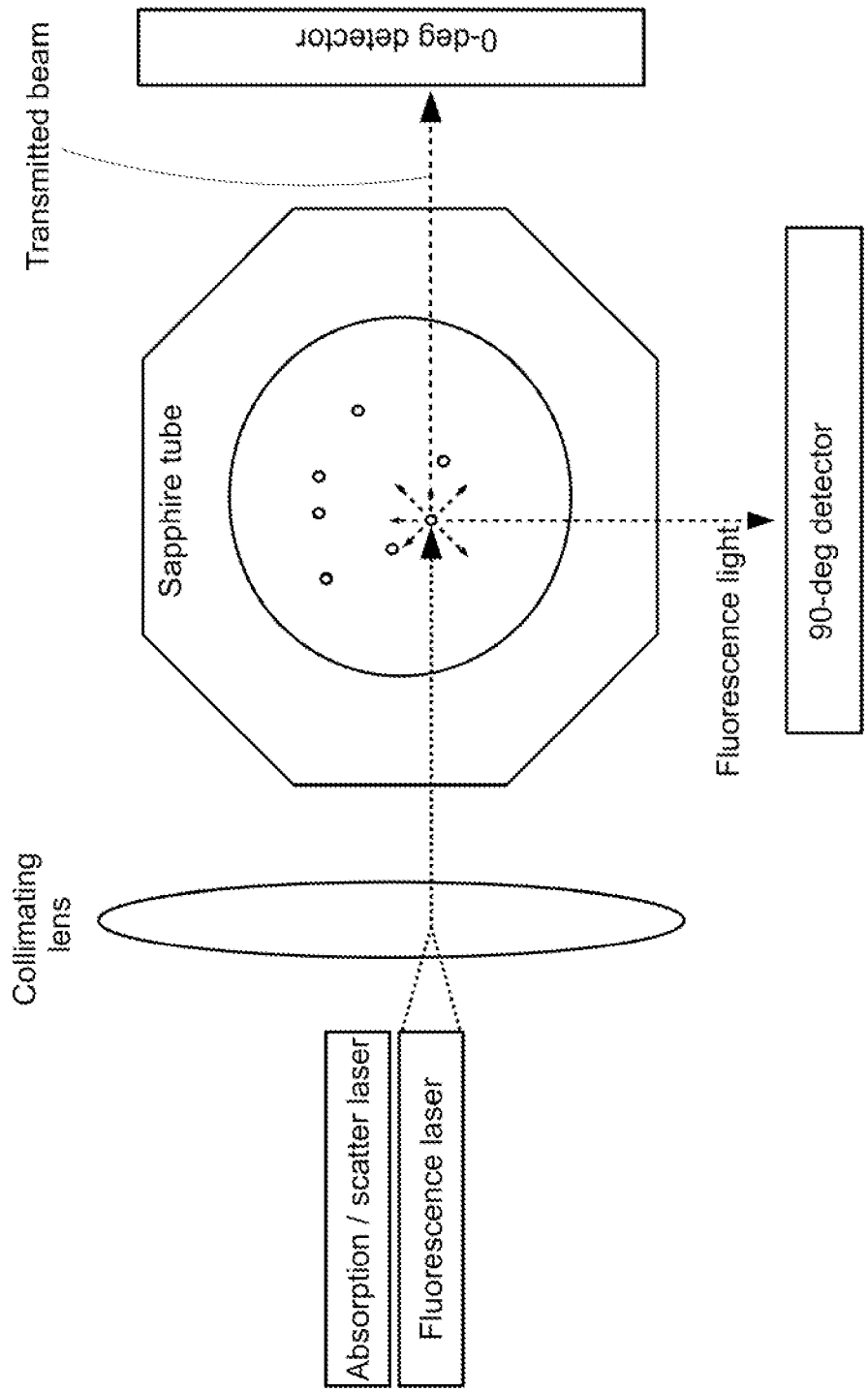
FIG. 5 is a schematic illustration of the method of the present invention.

FIG. 5 illustrates a simplified cross-sectional view of the apparatus FIG. 1 taken along the plane running vertical through the center of the apparatus while the apparatus is operating a second light mode. In this embodiment, the second light mode corresponds to the fluorescence light whose wavelength is also optimized for fluid mixture being studied. The wavelength is a selected fluorescence wavelength for desired excited fluorescence measurements. In the present embodiment of detecting high API oil-in-water, this light is operating in the ultraviolet (UV) blue light 400 nm range. Again, the collimating lens ensures the beam is parallel rays passing through the first side of the sapphire tube. When the excitation beam impacts an oil molecule in the water (whether free or dissolved), a stoke shift occurs and florescence light is emitted from the molecule in all directions. Some of the emitted light travels perpendicular to the original excitation beam and exits the sapphire tube through a third side adjacent the 90-degree detector. Likewise, some of the light of the beam is absorbed by the sample and a remaining portion of transmitted light travels straight and exits the sapphire tube adjacent to the 0-degree detector. The signal at the detector will be affected by the original light, the fluorescence, scattering, and the absorption from the fluid mixture.

FIG. 6 illustrates a block diagram of electrical components of the apparatus of FIG. 1 according to an exemplary embodiment. As shown, each of the fluorescence light and the absorption light includes a TEC that is monitored and controlled for a consistent temperature. Likewise, each of the lights includes a driver such as a digital-to-analog converter (DAC) for driving a light diode. Additional power components for the lights may be included as well; since these are well-known in the art, they have been omitted for brevity in FIG. 6. In this embodiment, the lights are mounted in the electronics housing of the apparatus and the light beam of the activated one(s) is/are passed to the light emission housing via a fiber optic cable connected between ports E and F.

Similar to the light circuits, each of the fluorescence detector and scatter detector is mounted on a TEC and includes TEC monitor/controller elements for maintaining a consistent temperature. The detectors include respective photosensitive diodes that are coupled to a transimpedance amplifier (TIA) and analog-to-digital converter (ADC).

Power, control signals, and results signals to/from the detectors are passed via cables connected between the detector housings and the electronics housing. For instance, port A on the electronics housing may be coupled to port C on the fluorescence detector housing, and port B on the electronics housing may be coupled to port D on the scatter detector housing.

In this embodiment, the apparatus further includes a plurality of other electronic components including a controller comprising one or more processors. The one or more processors may be included in a central processor unit (CPU) of a computer acting as the controller. In the following description the plural form of the word "processors" will be utilized as it is common for a CPU of a computer or other embedded computing device to have multiple processors (sometimes also referred to as cores); however, it is to be understood that a single processor may also be configured to perform the described functionality in other implementations.

The processors execute software instructions loaded from one or more storage devices and they may also store data such as results data in said storage device(s). The processors are further coupled to one or more communication interfaces allowing communications with other components such as the lights and detectors. Furthermore, the processors receive signals from sensors such as a temperature sensor for measuring a temperature of the fluid mixture flowing through the apparatus, a pressure sensor measuring a pressure of the fluid mixture flowing through the apparatus, and a flow sensor for measuring a flow rate of the fluid mixture flowing through the apparatus. The processors may also control one or more fans in the detectors and/or electronics housings to help maintain consistent temperatures.

Figure 7:
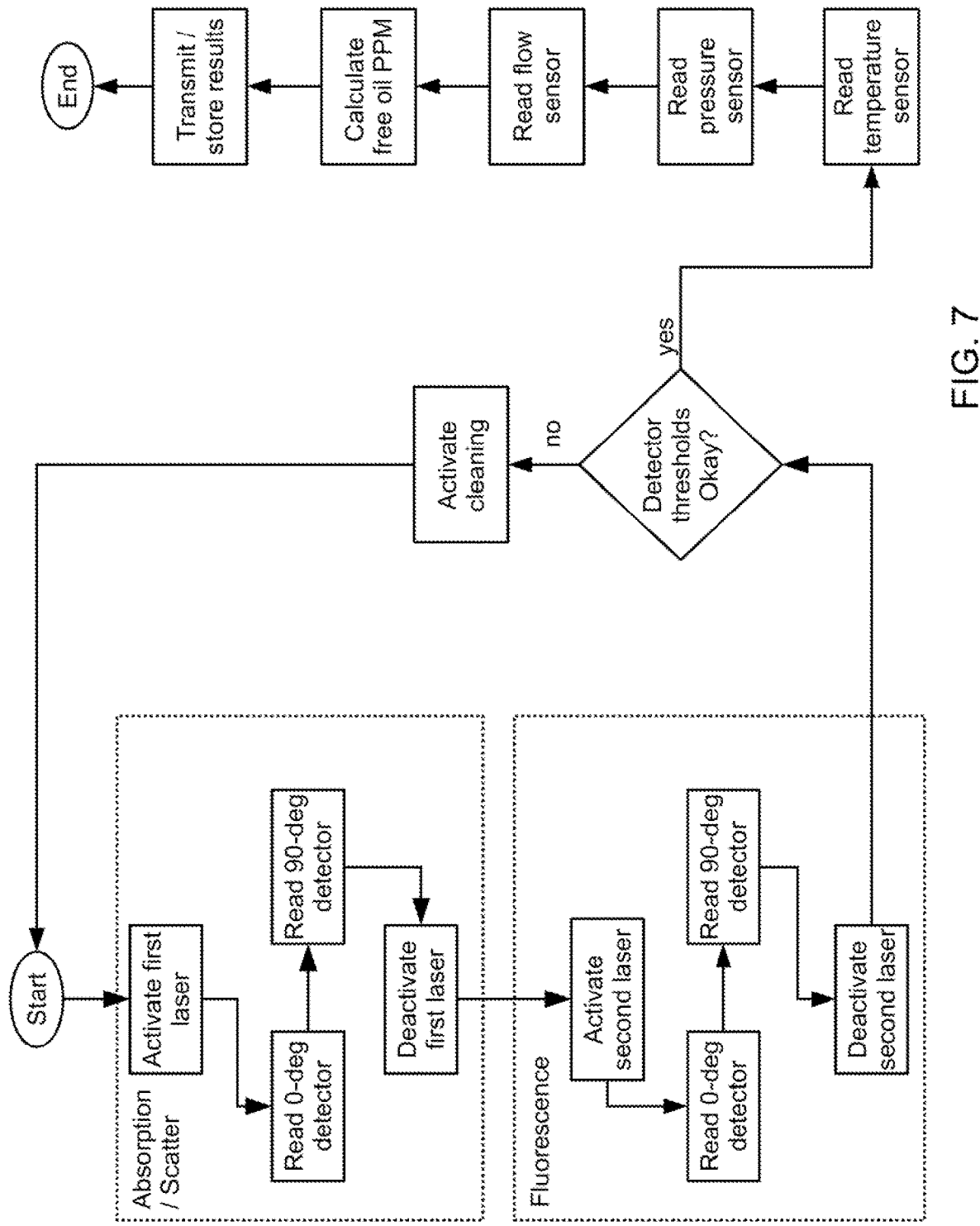
FIG. 7 is a schematic illustration of the method of the present invention.

FIG. 7 illustrates a flowchart of a method of measuring a quantify of oil in water utilizing the apparatus of FIG. 1 according to an exemplary embodiment. The steps of FIG. 7 may be performed by the one or more processors executing software loaded from the storage device in order to act as a controller of the apparatus. The steps of the flowchart are not restricted to the exact order shown, and, in other configurations, shown steps may be omitted or other intermediate steps added.

It bears repeating that the presence of TEC, ADC, AlN PCB, Fan etc. are for efficient operation of the measurement apparatus. The invention itself does not rely on the above. The crux of the invention here is utilizing the system of equations coming from the combination of fluorescence, scatter and absorption spectroscopy and automatic compensation for dirt buildup on the lens and mechanically clean the lens when the measurements fall below threshold.

The process starts by the controller activating the first light being the absorption/scatter light in this embodiment. Once the light is activated, the controller reads the results signals from both the 0-deg detector and the 90-deg detector and stores the results in the storage device. The controller then deactivates the absorption light.

The next phase of the process involves the controller activating the second light being the fluorescence light in this embodiment. The controller then reads the results signals from both the 0-deg detector and the 90-deg detector and stores the results in the storage device. The controller then deactivates the fluorescence light.

If the results thresholds over time are not okay meaning there is a build up a grime on the sapphire tube that is causing problems with the detected amplitudes of light, control proceeds to activate an automatic sapphire cleaning mechanism, described further below. If the detector thresholds are okay and cleaning is not required, control proceeds for the rest of the analysis.

For the rest of the analysis, the controller then reads the other sensor signals including temperature, pressure and flow rate. Given the coupled measurements from each spectroscopic light mode—fluorescence and scatter/absorption and other sensor information such as amount of lens coating, flow rate, pressure and temperature, the controller then calculates the amount of hydrocarbon in a mixture comprising of hydrocarbon and water, e.g. free oil in water. For instance, the oil amount may be calculated in parts-per-million (PPM) and the results are stored in the storage device and/or transmitted to an external device. In some embodiments, the external device is a portable computing device such as a mobile phone or other user device and the results are transmitted from the apparatus to the user device via a network such as a local area network (LAN) and/or the Internet.

Figure 9:
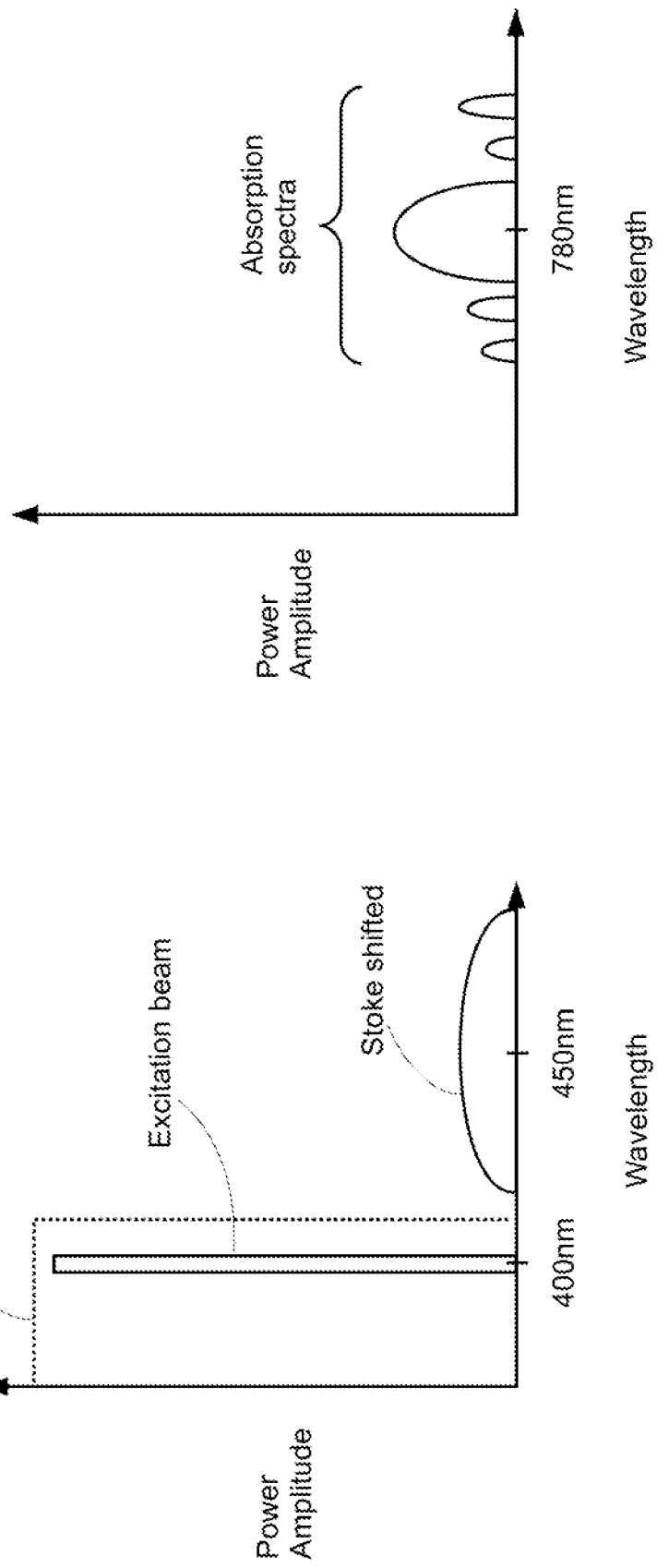
FIG. 9 is a schematic illustration of a spectral diagram showing how the results may be calculated and/or verified by the controller of the present invention.
Figure 8:
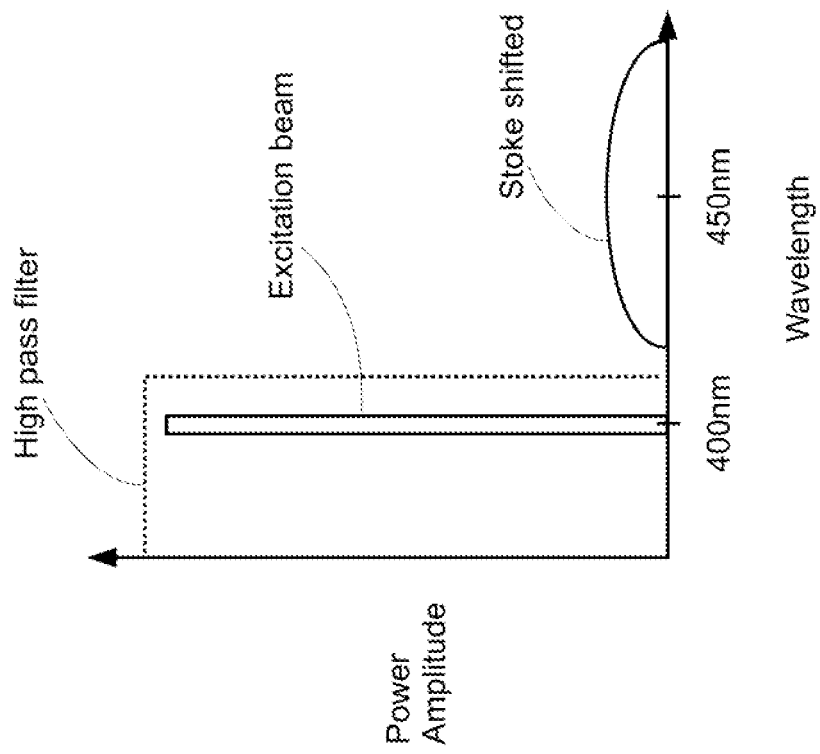
FIG. 8 is a schematic illustration of a spectral diagram showing how the results may be calculated and/or verified by the controller of the present invention.

FIGS. 8 and 9 illustrate spectral diagrams showing how the results may be calculated and/or verified by the controller. In FIG. 8, the fluorescence analysis involves using a high pass filter to thereby remove light in the range of the excitation beam from the results. The stoke shifted light approximately shifted upwards in wavelength by 50 nm can then be detected. When present in enough power amplitudes over sufficient periods of time (both can be detected by the processor utilizing respective thresholds), the controller will deem the fluorescence results to be positive. If the stoke shifted wavelengths are not found, the fluorescence results are deemed by the controller to be negative.

In FIG. 9, the absorption spectra is analyzed by the controller to determine whether it matches the expected absorption spectra for free oil. When the actual results match the expected results within a threshold margin of error, the controller deems the scatter results to be positive; otherwise, negative.

The positive/negative results of the two types of analysis, fluorescence and scatter/absorption, help the apparatus avoid false positives. For instance, if the results of both types of spectrographic modes are matching (positive), the results are highly likely to be correct. On the other hand, if the two types of analysis do not match (at least one is positive and one is negative), the amount of mismatch over time can help determine whether there are any false negatives or positives occurring. For instance, a high PPM oil in water as detected by the fluorescence detector may be deemed to be a false positive if the scanner/absorption analysis never detects any absorption spectra that matches free oil. On the other hand, if the scatter/absorption analysis detects a high PPM oil in water but the fluorescence analysis is negative, this is likely a false positive due to other contaminants in the water.

Figure 10:
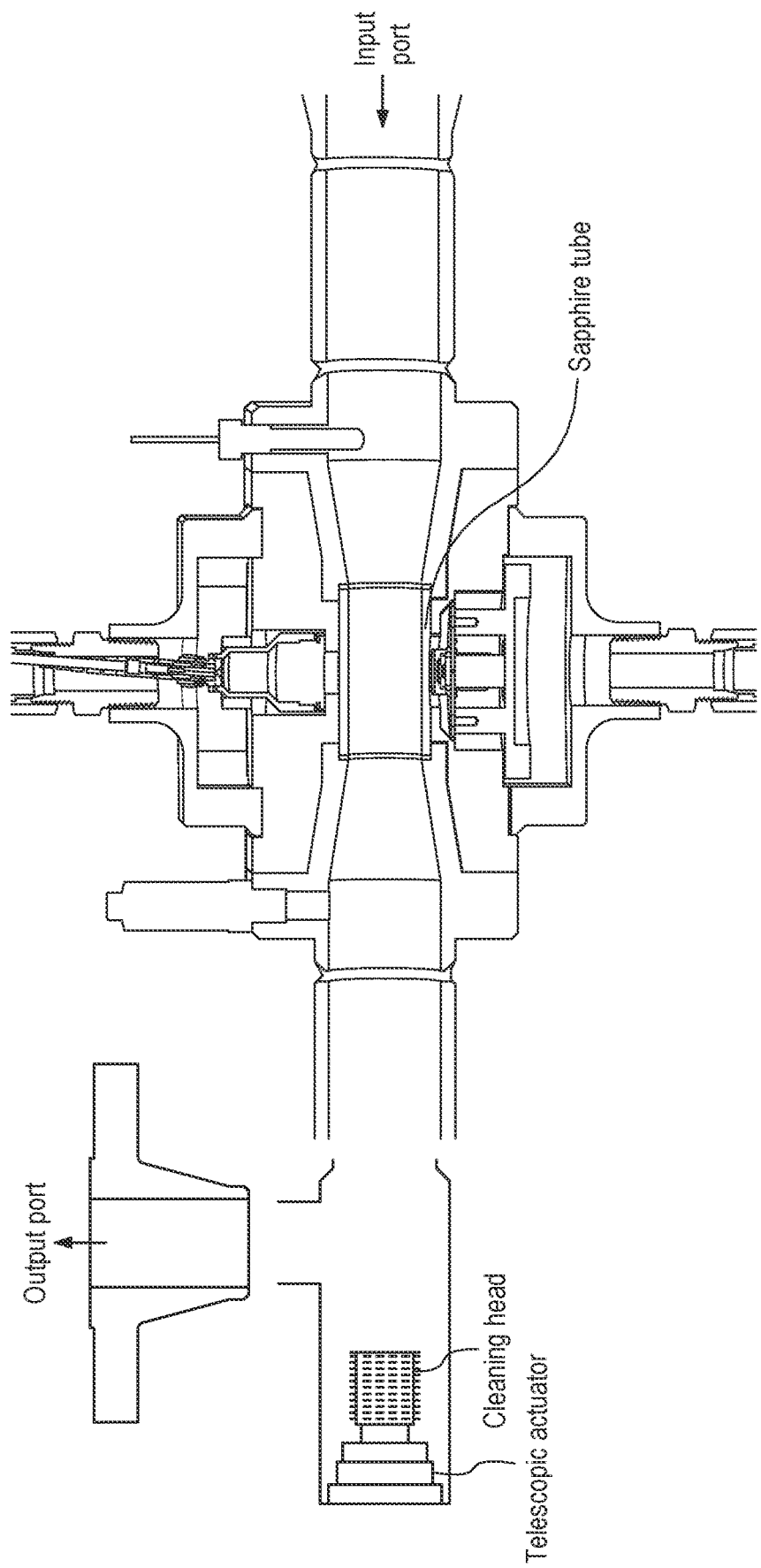
FIG. 10 is a cross-sectional view of an apparatus having an automatic sapphire tube cleaning mechanism in a retracted state according to an exemplary embodiment of the present invention.

FIG. 10 illustrates a cross-sectional view of an apparatus having an automatic sapphire tube cleaning mechanism in a retracted state according to an exemplary embodiment. As shown, in this embodiment, the input port is ninety degrees to the output port thereby allowing installation of a telescoping actuator and cleaning head in an end cavity of the apparatus.

FIG. 10 illustrates the telescoping actuator in the retracted state where it does not impede water flow from input to output port. The retracted state as illustrated in FIG. 10 is the normal operating state and oil in water analysis may be carried out as per the above description in this mode.

Figure 11:
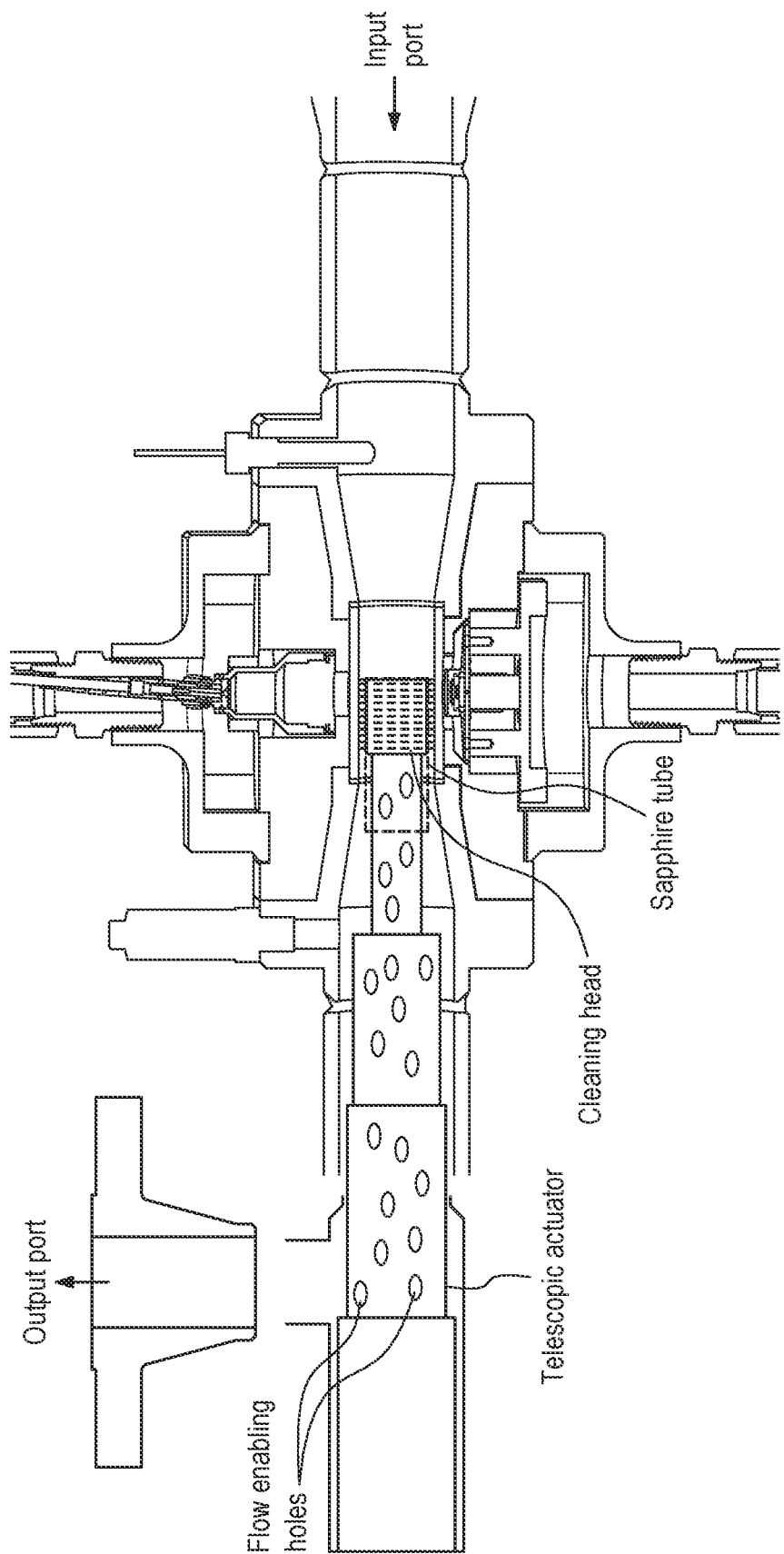
FIG. 11 is a cross-sectional view of the apparatus of FIG. 10.

FIG. 11 illustrates a cross-sectional view of the apparatus of FIG. 10 having the automatic sapphire tube cleaning mechanism in an extended state according to an exemplary embodiment. In some embodiments, either under control of the processors, a period timer such as a clock chip, or even when triggered from an external source, the telescoping actuator extends thereby pushing the cleaning head along the input port and into the sapphire tube. The fuzzy bristles of the cleaning head clean the inner circular surface of the sapphire tube preventing grime build up from interfering with the light from entering and exiting the water sample via said sapphire tube.

In this embodiment, the telescoping actuator is hollow and has a plurality of holes such that even when extended during cleaning it does not impede the flow of water and other fluids from the input port to the output port.

In some embodiments, the telescoping actuator is an electric linear actuator under control of the processors. Although electric and automatic cleaning is preferred; in some embodiments, the telescoping actuator is a manual device that can be extended under power of a human user on the outside of the apparatus.

Figure 12:
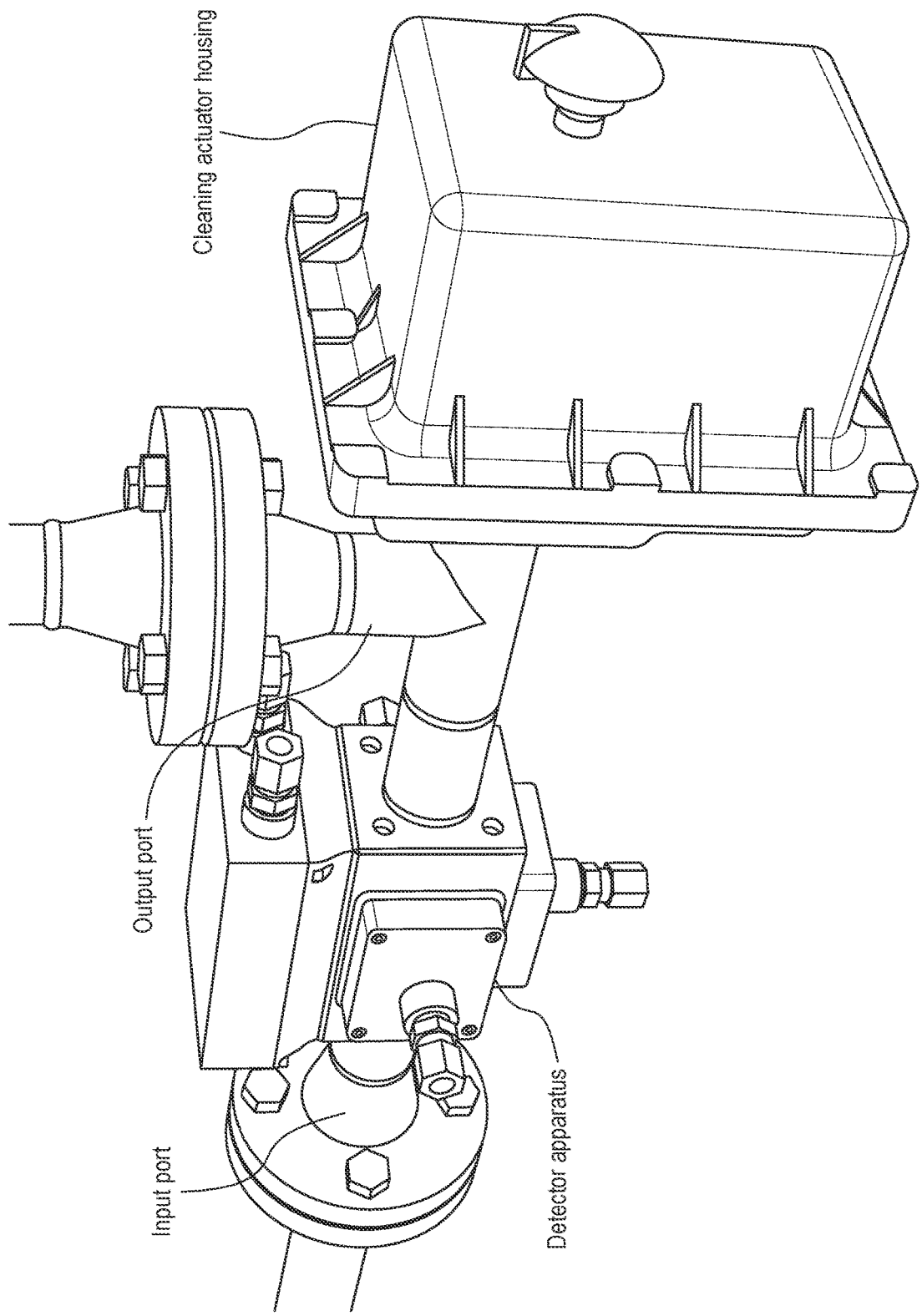
FIG. 12 is a perspective view of the outside of the apparatus.
Figure 15:
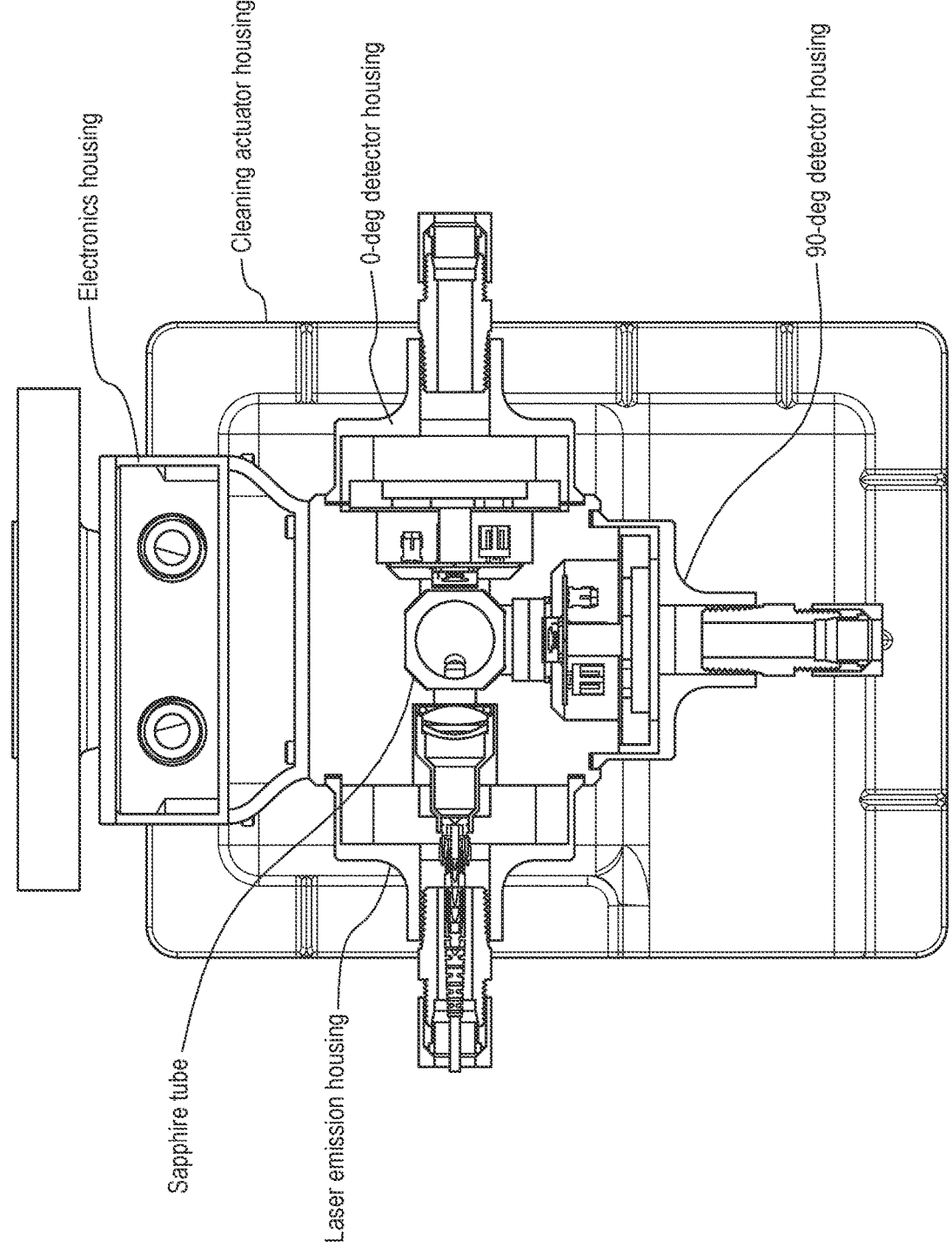
FIG. 15 is a sectional view of a third cross section of the embodiment of FIG. 12 taken along another vertical plane.

FIGS. 12 to 15 illustrate additional views of the apparatus of FIG. 10 including automatic cleaning actuator according to exemplary embodiments. In particular, FIG. 12 is a perspective view of the outside of the apparatus; FIG. 13 is a first cross section taken along the horizontal plane of FIG. 12; FIG. 14 is a second cross section taken along the vertical plane of FIG. 12; and FIG. 15 is a third cross section taken along a vertical plane of FIG. 12.

Typically, the mixture flows between two parallel windows: a first window through which the solution is irradiated by a light beam and a second window through which light emitted from the solution is passed to the detector. However, over time, these windows get coated by dirt, grime and other materials. As the windows become opaque from buildup of grime, fluorescence/scatter/absorption spectroscopy measurements will drift over time. The present invention monitors the transmitted intensity from the lens and automatically compensates for the effect of lens coating by correcting the measurements from the detectors.

Of course, over time, the lens coating may be too much, and the compensation would be unreliable because the detected signals will be too small. The apparatus determines that measurements from the first detector and the second detector are within a predetermined threshold to be sufficiently clean. When outside the threshold, a mechanical cleaning apparatus complements the automatic lens coating compensation scheme described above. There are some instruments which rely on ultrasonic cleaning of the lens; however, while ultrasonic cleaning may work for discrete solid particles and liquid droplets, it is not effective against some coatings such as grease, paraffins, asphaltenes etc.

The mechanical cleaner is automatically activated depending on measurements from a sensor which continuously monitors the amount of coating and dirt buildup on the lens. A manual override is provided for operator convenience. The cleaner is effective not only against solid particles coating the window but also against grease, paraffins, asphaltenes etc.

The combination of automatic coating compensation and mechanical cleaning apparatus allows for inline use of the analyzer, which distinguishes it from offline sample analyzers, with accompanying issues of proper sample gathering and preparation. The hydrocarbon concentration of the mixture flowing through a pipe is measured inline and in real-time.

Although the invention has been described in connection with preferred embodiments, it should be understood that various modifications, additions and alterations may be made to the invention by one skilled in the art without departing from the spirit and scope of the invention. For example, although the above description has focused on detecting free oil in water, the apparatus may also be utilized in a similar manner for other applications. For instance, the consequence of measuring fluorescence, scatter and absorption spectra is that this invention is not limited to detection of fluorescent chemicals.

Furthermore, the sapphire tube design allows for easy cleaning with a brush such as a pipe cleaner even if the brush is manually operated. Thus, embodiments such as FIG. 3 without automatic cleaning may also be beneficial.

Although it is beneficial to have dual light and detector to utilize both fluorescence and absorption spectroscopy for more reliable results, in some embodiments, easy cleaning of the tubular sapphire window and/or the automatic cleaning mechanism may be included in an apparatus with only a single type of spectroscopic analysis. In other words, in some embodiments, one of the fluorescence and absorption light/detector pairs are omitted.

The controller may be implemented by software executed by one or more processors operating pursuant to instructions stored on a tangible computer-readable medium such as a storage device to perform the above-described functions of any or all aspects of the controller. Examples of the tangible computer-readable medium include optical media (e.g., CD-ROM, DVD discs), magnetic media (e.g., hard drives, diskettes), and other electronically readable media such as flash storage devices and memory devices (e.g., RAM, ROM). The computer-readable medium may be local to the computer executing the instructions or may be remote to this computer such as when coupled to the computer via a computer network such as the Internet. The processors may be included in a general-purpose or specific-purpose computer that becomes the controller or any of the above-described modules as a result of executing the instructions.

In other embodiments, rather than being software modules executed by one or more processors, the controller may be implemented as hardware modules configured to perform the above-described functions. Examples of hardware modules include combinations of logic gates, integrated circuits, field programmable gate arrays, and application specific integrated circuits, and other analog and digital circuit designs.

Functions of single units may be separated into multiple units, or the functions of multiple units may be combined into a single unit. Unless otherwise specified, features described may be implemented in hardware or software according to different design requirements. All combinations and permutations of the above described features and embodiments may be utilized in conjunction with the invention.

The foregoing disclosure and description of the invention is illustrative and explanatory thereof. Various changes in the details of the illustrated structures, construction and method can be made without departing from the true spirit of the invention.

We claim:

1. A method for detecting, comprising the steps of:
installing an apparatus in a flowing medium, said flowing medium being comprised of free hydrocarbons, dissolved hydrocarbons, and solids,
wherein said apparatus comprises:
a fitting having an input end and an output end opposite said input end;
an input port at said input end;
an output port at said output end;

a sapphire tube having a hollow interior, said hollow interior being in fluid connection with said input port and said output port, said sapphire tube having a first outer side, a second outer side opposite said first outer side, and a third outer side between said first outer side and said second outer side;
a light emitter coupled to said first outer side;
a first detector coupled to said second outer side; and
a second detector coupled to said third outer side,
wherein said light emitter is comprised of a lens, an absorption and scatter wavelength emitter, and a fluorescence wavelength emitter parallel to said absorption and scatter wavelength emitter,
wherein said absorption and scatter wavelength emitter is positioned across from said first detector and offset to said second detector,
wherein said fluorescence wavelength emitter is positioned across from said first detector and orthogonal to said second detector, and
wherein said incident absorption and scatter beam is parallel to said incident fluorescence beam;
emitting said incident absorption and scatter beam through said sapphire tube from said absorption and scatter wavelength emitter;
absorbing said incident absorption and scatter beam;
scattering said incident absorption and scatter beam;
receiving said first absorption and scatter transmitted beam from said incident absorption and scatter beam with said first detector;
receiving said second absorption and scatter transmitted beam from said incident absorption and scatter beam with said second detector,
wherein said incident absorption and scatter beam has a selected absorption and scatter wavelength for targeted absorption measurements;
emitting said incident fluorescence beam through said sapphire tube from said fluorescence wavelength emitter;
exciting said free hydrocarbons and said dissolved hydrocarbon to generate said fluorescence excited beam;
receiving said fluorescence transmitted beam from said incident fluorescence beam with said first receiver;
receiving said fluorescence excited beam from said sapphire tube with said second receiver,
wherein said incident fluorescence beam has a selected fluorescence wavelength for desired excited fluorescence measurements; and
detecting said free hydrocarbons, said dissolved hydrocarbons and said solids, according to said selected absorption and scatter wavelength of said first absorption and scatter transmitted beam, said second absorption and scatter transmitted beam, said selected fluorescence wavelength of fluorescence transmitted beam, and said fluorescence excited beam.

2. The method for detecting, according to claim 1, wherein said apparatus further comprises:
an electronics housing being comprised of a central processing unit, said light emitter, said first detector, and said second detector being in communication with said central processing unit,
a temperature sensor in communication with said central processing unit,
a pressure sensor in communication with said central processing unit, the method further comprising the steps of:
collecting temperature sensor data and pressure sensor data with said central processing unit; and
calculating said free hydrocarbons, said dissolved hydrocarbons and said solids in said flowing medium.

3. The method for detecting, according to claim 1, wherein said incident absorption and scatter beam has a near infrared wavelength so as to determine free hydrocarbons and solids, and wherein said incident fluorescence beam has an ultra-violet wavelength so as to determine free hydrocarbons and dissolved hydrocarbons.

4. The method for detecting, according to claim 3, wherein the step of detecting said free hydrocarbons and said dissolved hydrocarbons comprises the steps of:
matching an increase in said first absorption and scatter transmitted beam and an increase in said fluorescence excited beam so as to confirm said free hydrocarbons, said dissolved hydrocarbons, and said solids.

5. The method for detecting, according to claim 3, wherein the step of detecting said free hydrocarbons and said dissolved hydrocarbons comprises the steps of:
mismatching a decrease in said first absorption and scatter transmitted beam and an increase in said fluorescence excited beam so as to confirm said dissolved hydrocarbons and said solids.

6. The method for detecting, according to claim 3, wherein the step of detecting said free hydrocarbons and said dissolved hydrocarbons comprises the steps of:
mismatching an increase in said first absorption and scatter transmitted beam and a decrease in said fluorescence excited beam so as to confirm said solids.

7. The method of claim 1, wherein said apparatus further comprises an ultra-violet filter on said second detector, said fluorescence excited beam being filtered for ultra-violet wavelengths.

8. The method for detecting, according to claim 7, wherein the step of detecting said free hydrocarbons and said dissolved hydrocarbons comprises the steps of:
matching an increase in said first absorption and scatter transmitted beam and an increase in said fluorescence excited beam at said second receiver so as to confirm said free hydrocarbons, said dissolved hydrocarbons, and said solids.

9. The method for detecting, according to claim 4, further comprising the step of:
switching said incident absorption and scatter beam to an ultraviolet wavelength from said near infrared wavelength so as to determine free hydrocarbons and solids, and wherein said incident fluorescence beam has an ultra-violet wavelength so as to determine free hydrocarbons and dissolved hydrocarbons; and
mismatching a decrease in said first absorption and scatter transmitted beam and an increase in said fluorescence excited beam so as to confirm said free hydrocarbons, said dissolved hydrocarbons, and said solids.

* * * * *

UNITED STATES PATENT AND TRADEMARK OFFICE
CERTIFICATE OF CORRECTION

PATENT NO. : 12,174,117 B2
APPLICATION NO. : 18/527064
DATED : December 24, 2024
INVENTOR(S) : David Farchy et al.

Page 1 of 1

It is certified that error appears in the above-identified patent and that said Letters Patent is hereby corrected as shown below:

On the Title Page

Item (73) Assignee, please replace "Agrar" with "Agar".

Signed and Sealed this
Third Day of June, 2025

Coke Morgan Stewart
*Acting Director of the United States Patent and Trademark Office*